(12) United States Patent
Engman et al.

(10) Patent No.: US 6,375,465 B1
(45) Date of Patent: Apr. 23, 2002

(54) BONE-ANCHORING ELEMENT

(75) Inventors: Fredrik Engman, Mölnlycke; Dan Lundgren, Hovås, both of (SE)

(73) Assignee: Nobel Biocare AB, Gothenburg (SE)

( * ) Notice: Subject to any disclaimer, the term of this patent is extended or adjusted under 35 U.S.C. 154(b) by 0 days.

(21) Appl. No.: 09/331,014

(22) PCT Filed: Jan. 19, 1998

(86) PCT No.: PCT/SE98/00075

§ 371 Date: Jul. 26, 1999

§ 102(e) Date: Jul. 26, 1999

(87) PCT Pub. No.: WO98/31296

PCT Pub. Date: Jul. 23, 1998

(30) Foreign Application Priority Data

Jan. 21, 1997 (SE) .............................................. 9700155

(51) Int. Cl.[7] .................................................. A61C 8/00
(52) U.S. Cl. ........................ 433/174; 433/172; 433/173
(58) Field of Search ................................ 433/172, 173, 433/174, 201.1

(56) References Cited

U.S. PATENT DOCUMENTS

| | | | |
|---|---|---|---|
| 4,122,605 A | 10/1978 | Hirabayashi et al. | |
| D353,674 S | 12/1994 | Jörnéus | |
| 5,399,090 A | 3/1995 | Padros-Fradera | |
| 5,482,463 A | * 1/1996 | Wilson, Jr. et al. | 433/173 |
| 5,533,898 A | * 7/1996 | Mena | 433/173 |
| 5,816,809 A | * 10/1998 | Sapkos | 433/173 |

FOREIGN PATENT DOCUMENTS

| | | |
|---|---|---|
| GB | 1291470 | 10/1972 |
| WO | WO 98/36701 | 8/1998 |

* cited by examiner

*Primary Examiner*—Nicholas D. Lucchesi
(74) *Attorney, Agent, or Firm*—Connolly Bove Lodge & Hutz, LLP

(57) ABSTRACT

A rotationally symmetrical anchoring element made of biocompatible material for anchoring into bone tissue. A circumferential surface includes a lower portion adapted to be incorporated with bone tissue and an upper portion that is located outside the bone tissue following implantation. The upper portion is adapted for attachment of a spacer piece or prosthetic structure thereto. The upper portion includes an unthreaded conical portion having a diameter that increases with increasing distance away from an upper end gable surface of the element. The conical portion forms a bearing surface for cooperation with a conical surface of the spacer piece or the prosthetic structure. The conical surface matching the conical portion. An external thread provided at a top of the upper portion secures the conical surface of the spacer piece or the prosthetic structure against the conical portion.

8 Claims, 3 Drawing Sheets

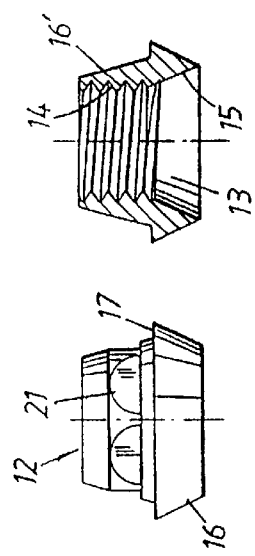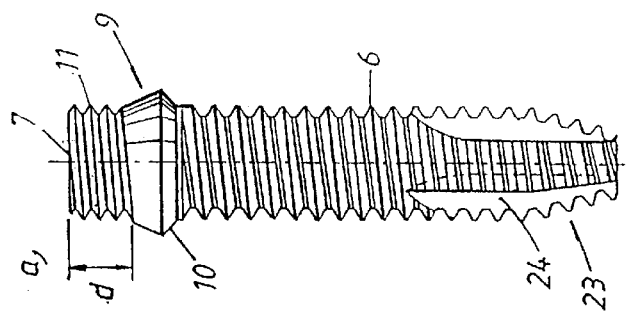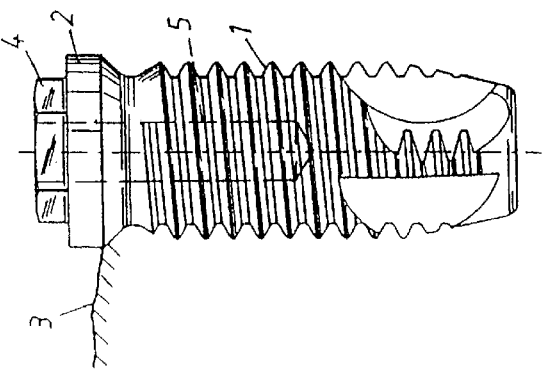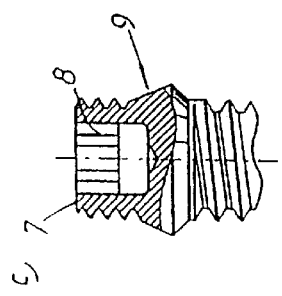

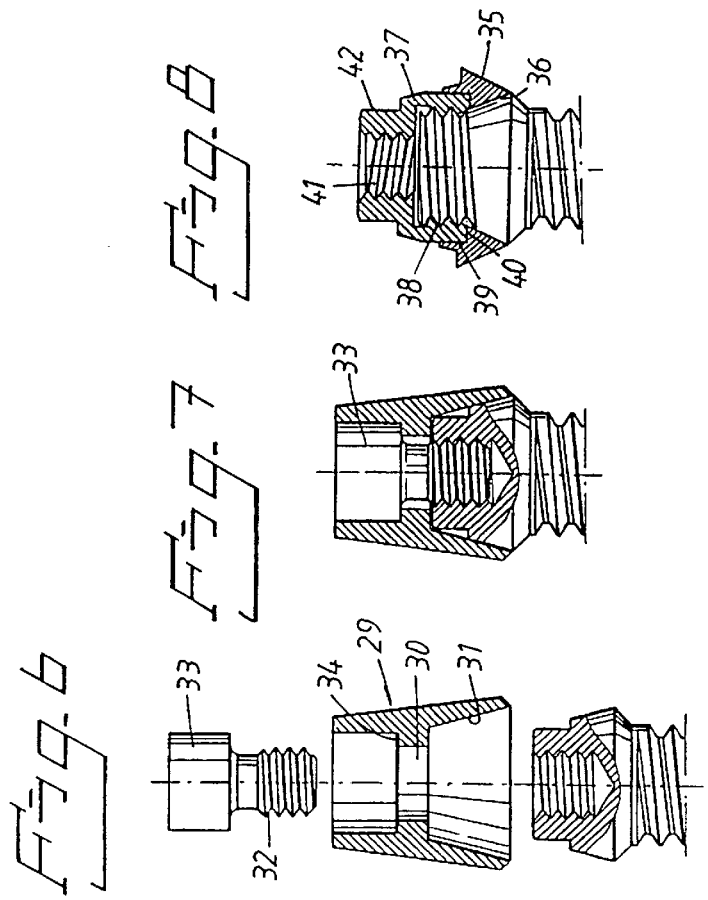
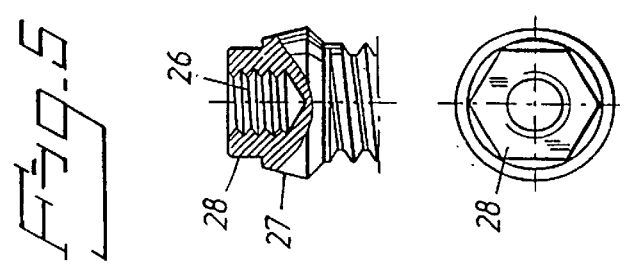
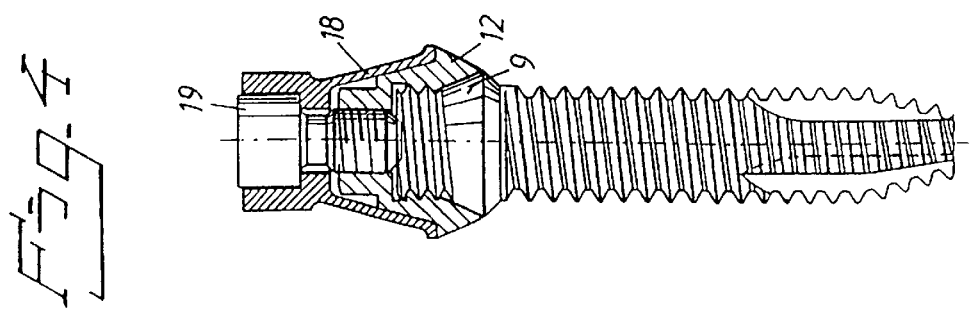

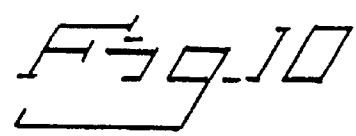
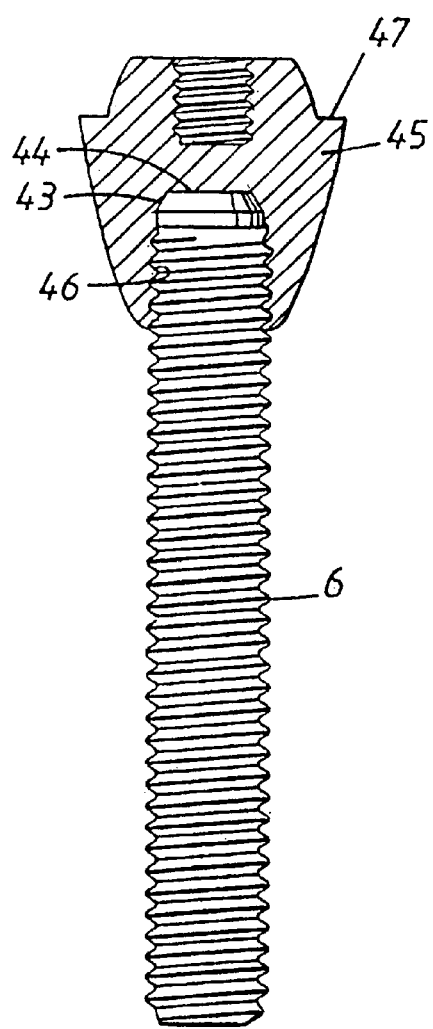
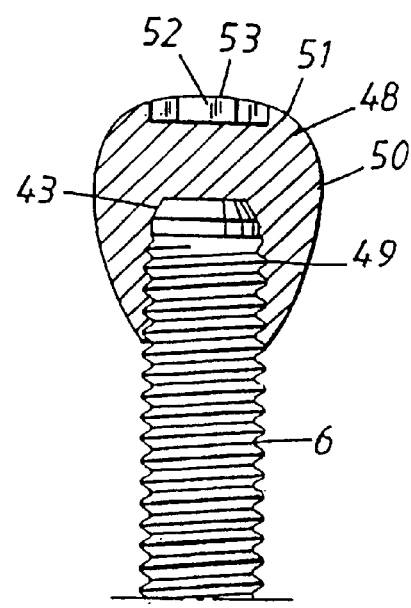

BONE-ANCHORING ELEMENT

FIELD OF THE INVENTION

The present invention relates to a rotationally symmetrical anchoring element (implant) for anchoring in bone tissue, for example for permanent anchoring of artificial teeth and dental bridges in the jaw bone. The anchoring element is made of a biocompatible material, for example titanium, and is intended for incorporation with bone tissue. Following implantation, the upper portion of the implant is located outside the bone tissue and is designed for the purpose of attachment thereto of a spacer piece or prosthetic structure.

It is already known to permanently anchor oral and extraoral prostheses in bone tissue with the aid of bone-anchoring elements made of titanium. To avoid loosening of the prosthesis, it is necessary to provide a healing-in period with direct contact, i.e. an exact match without intermediate connective tissue, between the anchoring element and the surrounding bone tissue. Such a direct contact between the bone-anchoring element and the surrounding bone tissue has been found to provided the best conditions for permanent anchoring of, for example, a tooth prosthesis.

The anchoring elements, which are in most cases screw-shaped, are surgically inserted into the jaw bone, specially prepared for this purpose, in a two-stage procedure, or the operation is performed in one stage. In the two-stage procedure, which has so far been the most suitable for jaw bone operations, the anchoring element is surgically inserted into the bone in a first operation. This is followed by an adequate healing-in period during which the upper end surface of the anchoring element is completely covered by intact mucous membrane. During the healing phase, the bone tissue grows firmly onto, and forms one unit with the implanted anchoring element. In a second operation the anchoring element is exposed, by having the mucous membrane surgically punctured, and an extension piece or spacer piece is attached to the anchoring element. When the operation is performed in one stage, the anchoring element is already initially allowed to penetrate the mucous membrane, and then the attachment to the spacer piece can be carried out, after a suitable healing-in period, without blood loss (without surgical intervention).

The spacer piece is generally attached to the anchoring element by means of a spacer screw which is screwed into a central, internally threaded bore in the anchoring element. Alternatively, the spacer piece can be cemented to the anchoring element via a screw or pin which runs down into the bore.

However, such a bore in the central attachment part of the anchoring element is a limiting factor in terms of its implantation. The internal bore represents a production step which increases costs, because the thread has to be cut to small dimensions with high precision.

In addition, the central bore inevitably entails a material reduction in the loaded part of the anchoring element. As a result there is an increased risk of fracturing unless this is compensated for in an appropriate way, generally by making the anchoring element thicker than would otherwise be the case. The anchoring element is thus given a minimum diameter below which, for reasons relating to strength, it is not possible to go, because of the forces to which the element is exposed in, for example, the jaw bone during mastication.

It has also been proposed to attach a prosthetic structure directly to the anchoring element without any intermediate spacer piece, for example in Swedish Patent Application 95.03291-8 of Dan Lundgren. One advantage of such a solution is that it requires one component less. Also, the central bore in the upper part of the anchoring element can be made with a smaller diameter, which permits introduction of slightly narrower anchoring elements without any risk of fracturing on account of the fact that the material thickness is too small in the wall between the central bore and the circumferential surface of the anchoring element. However, even though the bore can be made with a smaller diameter, it is still necessary, even in this case, to have a bore which reduces the material thickness and therefore inevitably limits the smallest critical diameter of the anchoring element.

There are many reasons why it is desirable to use narrower anchoring elements. Such elements can be used in bone areas where the available bone width is much smaller than before. There are a number of such applications in which the available bone width has been too small to allow present-day implants to be used in a clinically reliable manner because these implants have been too thick.

It is already known to design a bone-anchoring element without an upper bore and with a nut-like sleeve applied to the threaded circumferential surface, see U.S. Pat. No. 4,122,605 of Hirabayashi et al. The sleeve n is threaded onto the anchoring element to the desired position so as to bear against the bottom surface of a bore 6 in the bone surface $b_1$. The prosthetic structure in the form of a tooth is then connected to the sleeve by means of cement 4. The aim of this arrangement is quite different, however, namely to provide a counter force to the bone in order to increase stability.

Although such a construction should in theory make it possible to use narrower fixtures, its practical application is limited. If the nut-like sleeve were to function as the spacer piece, then this would not have any exact position in relation to the screw-shaped circumferential surface, with all the disadvantages that this entails, and the open, nut-like sleeve obviously only permits cemented solutions.

SUMMARY OF THE INVENTION

One object of the present invention is to make available an anchoring element which simplifies the implantation, for example reduces the number of components required, and which affords advantages in terms of production engineering, and in which the attachment between anchoring element and spacer piece can be formed by a screw connection, with the flexibility which characterizes such a connection.

Another object of the invention is to make available a tighter connection in order to reduce the risk of bacterial invasion and inflammatory infiltrates in the soft tissue which surrounds the joint between the two implant parts.

Yet another object of the invention is to make available an anchoring element which can be made to heal into bone areas of much smaller bone width than has previously been possible, without any risk of loosening or fracturing of the anchoring element, and which element dose not have the disadvantages discussed above in connection with Hirabayashi et al.

According to the invention, this is achieved by means of the fact that the anchoring element has the features that include the upper portion of the circumferential surface, designed for attachment of the spacer piece or of the prosthetic structure, and including a smooth (unthreaded) conical portion whose diameter increases in the direction away from the upper end surface (gable surface) of the element, this conical portion forming a bearing surface for the spacer piece or the prosthetic structure.

An anchoring element designed in this way affords several advantages:

The anchoring element is easier to implant since it includes one component less for the spacer attachment.

The anchoring element is simple to produce.

The anchoring element can be implanted in jaws with dental crests of very small (buccolingual) bone width.

The anchoring elements can be placed tighter together in the mediodorsal direction of the dental crest than has been possible with traditional anchoring elements.

The anchoring elements can often be placed between the mandibular arch and the lingual, and in some cases also the buccal, bone surface of the lower jaw.

The positioning between mandibular arch and buccal/ lingual bone surface means that two anchoring elements can sometimes be placed in the same buccolingual cross-section instead of one. This provides, overall, the same stability as in the case of one thicker anchoring element in the same region.

The positioning of the narrower implants means that these, to a greater extent than the thicker ones, can be placed in compact bone instead of in cancellous (high-mesh) bone, which increases their contact surface with the surrounding bone.

The small diameter of the anchoring elements means that they can be placed at several locations where there is limited lateral bone space.

The anchoring elements can also be placed in the tops of the interalveolar bone septa during or after extraction of teeth, so that they can be used as temporary or permanent direct implants.

The surgical technique is simplified because it is possible to use a one-stage technique and cutting of edges can be dispensed with.

There is no need for lifting large flaps, which increases patient comfort, saves the jaw bone and makes the intervention easier.

The joint between the anchoring element and the spacer piece or prosthetic structure can be made hermetically tight, or can be omitted altogether, in the alternative embodiments in which implant and spacer piece constitute one continuous piece. This eliminates the risk of bacterial invasion and inflammatory infiltrates in the soft tissue surrounding the joint.

Because the spacer piece can be adapted in terms of its height to the thickness of the soft tissue, an optimum aesthetic appearance can be obtained.

Because the anchoring element can have a small diameter and thus requires very little space, it is also well suited for use in orthodontic treatment (correction of the teeth), i.e. step by step adjustment of the teeth using relatively small forces.

BRIEF DESCRIPTION OF THE DRAWINGS

The present invention will be described in greater detail hereinafter with reference to the attached drawings, in which:

FIG. 1 shows, in a side view, a traditional screw-shaped anchoring element (implant) in a standard design, FIG. 2 shows, in a side view and in a view from directly above, a screw-shaped anchoring element according to the invention, FIG. 3 shows examples of different spacer pieces for the anchoring element, FIG. 4 shows the anchoring element provided with such a spacer piece and a so-called gold cylinder for attachment of a prosthetic structure, FIG. 5 shows an alternative embodiment of the spacer attachment part of the anchoring element, FIG. 6 shows a spacer piece with spacer screw for such an anchoring element, FIG. 7 shows anchoring element and spacer piece joined together, FIG. 8 shows a spacer element which consists of an external spacer sleeve and an internal threaded locking sleeve, FIG. 9 shows another example of how anchoring element and spacer piece can be designed, and FIG. 10 shows such an anchoring element provided with a cover element.

DETAILED DESCRIPTION OF THE PREFERRED EMBODIMENT(S)

The known anchoring element (implant) shown in FIG. 1 is made of titanium or another biocompatible material. It has a screwthreaded portion 1 which is screwed into a hole that has been prepared beforehand (drilled) in the bone, in a way that its end surface 2 comes to lie approximately leveled with the bone surface, which has been indicated by 3 in the figure. The implant has an external tool grip in the form of a hexagonal portion 4 at its upper part, and a threaded hole (bore) 5 for attachment of an extension piece or spacer piece when implementing the two-stage procedure described in the introduction. In this procedure the anchoring element is covered, during the healing-in period, by a cover screw screwed tightly into the said bore 5.

FIG. 2a shows a corresponding side view of an anchoring element (implant) according to the invention. Also in this case the element has an external screwthreaded circumferential surface 6, but does not have an internal bore for attachment of a spacer piece or prosthetic structure. Instead, the end surface (gable surface) 7 of the anchoring element is provided with an internal tool grip in the form of a screwdriver slot, internal hexagon or other internal tool grip 8, for example according to Swedish Patent Application 96.03477-2, Jörnéus et al., for engagement of a tool adapted for screwing the anchoring element into a hole made in the bone, see FIG. 2b which shows the anchoring element from directly above, and FIG. 2c which shows a cross-section through the upper part of the anchoring element.

At the top, near to the gable surface 7, the screw-shaped circumferential surface merges into a smooth, unthreaded portion 9 which can be between 0.5 mm and 5 mm, but preferably between 1 and 2 mm, in length. The unthreaded portion 9 is conically shaped and converges in the direction towards the gable surface 7. The cone angle can vary within wide limits, but preferably lies between 5° and 30°. Between the screw-shaped circumferential surface and the converging portion there is in this case, which represents a narrower anchoring element, an intermediate diverging portion 10 which forms a transition between the cylindrical, threaded circumferential surface and the conical portion 9.

The conical portion of the circumferential surface is located close to the gable surface 7 of the anchoring element, but expediently at a slight distance d from the gable surface so that an external threaded portion 11 is also situated between the smooth conical portion 9 and the gable surface 7.

The anchoring element is made of a material which has a sufficient degree of biocompatibility and strength to serve permanently as a bone anchor for prosthetic structures in the form of crowns, bridges and other prostheses. These can be made of ceramics, metal, or tissue-compatible plastic, or combinations thereof.

Different combinations of material can be used for different indications. For example, when, for reasons of space limitations, the anchoring element has to be given an extremely small volume, it can have a core of especially strong alloys and a coating of pure titanium and/or hydroxyapatite in order to increase the strength of the anchoring element, while at the same time the bonding to the surrounding bone is optimized. The anchoring element can also be coated in a known manner with some type of growth factor which stimulates rapid bone formation and thus improves the element's ability to take.

A spacer piece 12 is designed in such a way that it can be attached to the neck portion of the anchoring element, see FIG. 3. The spacer piece is designed as a sleeve with, in this case, a through-channel 13 which has, in its outer portion, an internal thread 14 matching the thread on the circumferential surface of the anchoring element, and, in its inner portion, a smooth-finished, conical surface 15 matching the conical part 9. This arrangement permits a tight attachment between the anchoring element and the spacer piece. The frictional forces between the two congruent, smooth-finished circumferential surfaces can be adjusted, on the one hand as a function of the tightening force or choice of material and, on the other hand, as a function of the angle of convergence of the surfaces. If this angle is sufficiently small, the two components can be tighetened so hard that it is practically impossible to distinguish them (cold-welding).

The external profile of the spacer piece consists of a lower part 16 which diverges conically towards the gable surface and which, after attachment to the anchoring element, forms an extension of the transition portion 10, and of an outer part 16' narrowing conically towards the gable surface. Between these two parts there is an annular shoulder 17 against which the base of a conical, so-called gold cylinder 18 is intended to bear. Conical gold cylinders of this type are already known and normally form part of the prosthetic structure, see for example U.S. Des. No. 353,674, and are therefore not described in any detail here. The gold cylinder 18 is attached to the spacer sleeve by means of a locking screw 19 whose thread is matched to the internal thread 14 of the spacer sleeve.

Alternatively, the through-channel 13 can consist of two threaded bores of different diameters, on the one hand a wider part 14' matching the thread of the circumferential surface of the anchoring element, and a narrower part 20 for a narrower locking screw 19, as is shown in FIG. 3b.

The external, conically narrowing part of the spacer sleeve is expediently provided with plane engagement surfaces 21 for a tightening tool used for attaching a prosthesis, in order to prevent the tightening torque from being transmitted onwards to the anchoring element.

In the variant which is shown in FIG. 3b, the upper part of the spacer sleeve is provided with an engagement portion, for example a hexagon 22, for a corresponding tightening tool.

In FIG. 4, the anchoring element is shown with spacer sleeve 12 and gold cylinder 18 both fitted.

The diameter of the anchoring element can vary from several tenths of a millimetre upwards, depending on the area of application. A normal dimension would probably be 1 mm for orthodontic anchoring for correction of teeth, while 2 to 3 mm would probably be a normal dimension for anchoring of prosthetic structures, although greater dimensions may be considered.

The design of the tip 23 of the anchoring element does not form part of the present invention and is therefore not described in detail. It can be, for example, self-tapping and have three symmetrically arranged channels 24 with cutting edges, as is shown diagrammatically in FIG. 2.

Instead of an external thread for attachment of a spacer piece, the anchoring element can have an upper bore 26 with internal thread, as shown in FIG. 5. In contrast to a traditional anchoring element (as is shown in FIG. 1), this bore 26 does not extend down into the loaded, threaded zone, but only in the upper conical portion 27. At the top, this portion has an external tool grip in the form of a hexagon 28.

FIG. 6 shows a spacer piece 29 which is to be attached to the anchoring element. The spacer piece 29 is designed as a sleeve with a through-channel 30 whose lower part, directed towards the anchoring element, has a conical surface 31 congruent with the conical portion 27 of the anchoring element. Therfore also in the embodiment, a tight connection is obtained between the anchoring element and the spacer piece.

The spacer piece 29 is attached to the anchoring element by means of a spacer screw 32 which is screwed down into the bore 26 and whose head 33 bears against an internal shoulder 34 in the channel 30.

FIG. 7 shows the parts joined together.

FIG. 8 shows a spacer piece which consists of two parts, on the one hand an external spacer sleeve 35 with an internal conical surface 36 which is secured on the conical portion of the anchoring element in the same way as in the previously described embodiments, and on the other hand an internal locking sleeve 37 with an internal thread 38 for attachment to the upper attachment thread 11 of the anchoring element. The internal locking sleeve extends down into an annular recess 39 in the spacer sleeve 35 and bears with its base portion against the bottom 40 of the recess. At the top, the locking sleeve has an internal thread 41 for a locking screw for prosthesis attachment. The spacer sleeve 35 can be made, for example, of titanium, like the anchoring element, while the locking sleeve can be made of gold.

The two-part spacer piece can be used in those cases where a rotationally fixed spacer pillar is required, for example in the case of spacer sleeves with asymmetrical external geometry (oval, elliptic or the like) or in the case of angled spacers. By tightening the locking sleeve 37 on the spacer sleeve 35, this can be fixed in a defined rotational position. The external, upper portion of the locking sleeve has, for this purpose, a tool grip in the form of a hexagon 42.

FIGS. 9 and 10 show a pair of alternative embodiments of an anchoring element according to the invention. The conical attachment surface 43 is in this case located at the very top adjacent to the gable surface 44 of the anchoring element. The spacer piece 45 in this case has a bore 46 with an internal conical smooth surface which is congruent with the conical attachment surface 43 of the anchoring element, and an external part with an internal thread which matches the thread of the circumferential surface. The spacer piece has an annular shoulder 47 against which a gold cylinder in the prosthetic structure is intended to bear.

A cover screw 48 is attached to the neck portion of the anchoring element during the healing-in period, see FIG. 10, this cover screw being provided with a bottom hole 49 and an external neck portion 50 congruent with that located on the spacer piece or alternatively the prosthetic structure which is to be attached to the anchoring element. The upper (coronal) portion 51 of the cover screw is gently rounded and is provided with an internal hexagon arrangement 52 to permit screwing and unscrewing of the cover screw with a hexagon wrench. The cover screw preferably has such a low profile that its top 53 lies leveled with or immediately above the mucous membrane.

The invention is not limited to the examples which have been described above, but can be varied within the scope of the attached patent claims. Thus, it will be appreciated that the anchoring element can be used for both two-stage and one-stage procedures for implantation in bone tissue.

What is claimed is:

1. A rotationally symmetrical anchoring element made of biocompatible material for anchoring into bone tissue, comprising:

a circumferential surface comprising lower portion adapted to be incorporated with bone tissue;

an upper portion that is located outside the bone tissue following implantation, the upper portion adapted for attachment of a spacer piece or prosthetic structure thereto, the upper portion including an unthreaded conical portion having a diameter that increases with increasing distance away from an upper end gable surface of the element, the conical portion forming a bearing surface for cooperation with a conical surface of the spacer piece or the prosthetic structure, the conical surface substantially matching the conical portion; and an external thread provided at a top of the upper portion for securing the conical surface of the spacer piece or the prosthetic structure against the conical portion.

2. The anchoring element according to claim 1, wherein the upper end gable surface is provided with an internal tool grip.

3. The anchoring element according to claim 1, wherein the circumferential surface is screw-shaped, with an external thread intended to be screwed into bone tissue, the conical portion being located on the circumferential surface at a distance from an upper end surface of the anchoring element.

4. The anchoring element according to claim 1 wherein a conical portion is located at a very top adjacent to the gable surface of the anchoring element, the upper part of the thread of the circumferential surface constituting an attachment thread for a spacer piece.

5. The anchoring element according to claim 1, wherein a cone angle of the conical portion lies between 5° and 30°.

6. The anchoring element according to claim 1, further comprising:

a spacer piece comprising an internal conical surface and an internal thread, the conical surface being complementary with the external conical bearing surface of the anchoring element so as to provide a tight seal when the spacer piece is secured on the anchoring element, the internal thread cooperating with the external thread of the upper portion of the anchoring element when the spacer piece is secured on the anchoring element.

7. The spacer piece according to claim 6, the spacer being secured on the conical bearing surface of the anchoring element via a separate locking sleeve which engages with the upper attachment thread of the anchoring element.

8. A spacer piece for attachment to an anchoring element having an external conical bearing surface and an upper end gable surface having a central bore, the spacer piece comprising:

a lower end surface;

an upper end surface;

an outer circumferential surface having a decreasing diameter from the lower end surface to the upper end surface;

an inner, unthreaded bore extending up to the upper end surface;

an internal conical having a shape complementary to the external bearing surface of the anchoring element so as to provide a tight seal when the spacer piece is secured on the anchoring element;

an inner shoulder in an upper end; and a separate spacer screw for securing the spacer element on the conical bearing surface on the anchoring element, the spacer screw engaging the central bore in the gable surface of the anchoring element, the spacer screw comprising a screw head that bears against the inner shoulder of the spacer piece.

\* \* \* \* \*